United States Patent [19]
Waller et al.

[11] Patent Number: 5,362,769
[45] Date of Patent: Nov. 8, 1994

[54] ORTHODONTIC ADHESIVES

[75] Inventors: Duncan E. Waller, Ypsilanti, Mich.; Raymond F. Wong, Chino Hills, Calif.

[73] Assignees: Ormco Corporation, Glendora, Calif.; Kerr Manufacturing Co., Romulus, Mich.

[21] Appl. No.: 879,568

[22] Filed: May 7, 1992

[51] Int. Cl.$^5$ .................. A61K 6/08; C08K 5/02; C08F 2/46; C08F 118/02
[52] U.S. Cl. .................. 523/116; 523/118; 524/462; 522/13; 522/14; 522/17; 522/36; 526/274; 526/319; 526/329.5
[58] Field of Search .................. 523/116, 118; 522/13, 522/14, 17, 36; 524/462; 526/274, 319, 329.5

[56] References Cited

U.S. PATENT DOCUMENTS

| | | | |
|---|---|---|---|
| 3,223,681 | 12/1965 | Rambosek | 260/775 |
| 3,327,016 | 6/1967 | Lee, Jr. | 260/830 |
| 3,629,187 | 12/1971 | Waller | 260/41 R |
| 3,709,866 | 1/1973 | Waller | 260/27 R |
| 3,729,313 | 4/1973 | Smith | 96/27 R |
| 3,839,065 | 10/1974 | Overhults et al. | 260/30.6 |
| 3,931,678 | 1/1976 | O'Sullivan et al. | 32/15 |
| 4,010,545 | 3/1977 | Kilian et al. | 32/14 A |
| 4,063,360 | 12/1977 | Waller | 32/14 A |
| 4,071,424 | 1/1978 | Dart et al. | 204/159.15 |
| 4,089,763 | 5/1978 | Dart et al. | 204/159.23 |
| 4,097,994 | 7/1978 | Reaville et al. | 32/15 |
| 4,110,184 | 8/1978 | Dart et al. | 204/159.23 |
| 4,123,416 | 10/1978 | Potter et al. | 260/42.18 |
| 4,131,729 | 12/1978 | Schmitt et al. | 526/282 |
| 4,148,988 | 4/1979 | Masuhara et al. | 526/318 |
| 4,180,913 | 1/1980 | Takeuchi et al. | 433/228 |
| 4,189,365 | 2/1980 | Schmitt et al. | 204/159.23 |
| 4,192,795 | 3/1980 | Madhaven et al. | 260/42.52 |
| 4,220,582 | 9/1980 | Orlowski et al. | 260/42.28 |
| 4,221,698 | 9/1980 | Lee, Jr. et al. | 260/42.52 |
| 4,243,478 | 6/1981 | O'Sullivan et al. | 260/42.52 |
| 4,252,526 | 2/1981 | Madhaven et al. | 433/228 |
| 4,259,075 | 3/1981 | Yamauchi et al. | 433/217 |
| 4,259,117 | 3/1981 | Yamauchi et al. | 106/35 |
| 4,284,551 | 8/1981 | Argentar | 260/42.43 |
| 4,288,221 | 9/1981 | Engel | 433/202 |
| 4,302,381 | 12/1981 | Omura et al. | 260/42.15 |
| 4,304,893 | 4/1982 | Orlowski | 526/309 |
| 4,323,348 | 4/1982 | Schmitz-Josten et al. | 433/228 |
| 4,340,529 | 7/1982 | Lee, Jr. et al. | 524/105 |
| 4,340,532 | 7/1982 | Lee, Jr. et al. | 524/854 |
| 4,347,174 | 8/1982 | Nagase et al. | 523/116 |
| 4,368,043 | 1/1983 | Yamauchi et al. | 433/217 |
| 4,372,836 | 2/1983 | Schmitt et al. | 204/159.23 |
| 4,375,967 | 3/1983 | Schaefer | 433/199 |
| 4,386,912 | 6/1983 | Nagase et al. | 433/228 |
| 4,388,421 | 6/1983 | Suzuki et al. | 523/118 |
| 4,394,403 | 7/1983 | Smith | 427/42 |
| 4,394,465 | 7/1983 | Podszun et al. | 523/116 |
| 4,406,625 | 9/1983 | Orlowski et al. | 433/228 |
| 4,411,625 | 10/1983 | Koblitz et al. | 433/217 |
| 4,426,504 | 1/1984 | Nandi | 526/282 |
| 4,437,836 | 3/1984 | Schmitz-Josten et al. | 433/199 |
| 4,439,380 | 3/1984 | Michl et al. | 264/16 |
| 4,449,938 | 5/1984 | Pollak | 523/116 |
| 4,459,193 | 7/1984 | Ratcliff et al. | 204/159.23 |
| 4,479,782 | 10/1984 | Orlowski et al. | 433/220 |
| 4,491,453 | 1/1985 | Koblitz et al. | 433/217 |
| 4,503,169 | 3/1985 | Randkiev | 523/117 |
| 4,504,231 | 3/1985 | Koblitz et al. | 433/228 |
| 4,514,174 | 4/1985 | Dougherty et al. | 433/226 |

(List continued on next page.)

FOREIGN PATENT DOCUMENTS 687299 2/1953 United Kingdom .

Primary Examiner—Paul R. Michl
Assistant Examiner—La Vonda DeWitt
Attorney, Agent, or Firm—Wood, Herron & Evans

[57] ABSTRACT

The present invention is directed to orthodontic adhesive formulations, both light curable in the visible wavelength range, and self-curing, for use in the adherence of orthodontic appliances to the surface of etched human teeth. These formulations exhibit a high degree of surface wetting, an available source of leachable fluoride, low polymerization shrinkage, high physical properties and adhesion, and in the light curable embodiment, a post-curing capability.

17 Claims, No Drawings

U.S. PATENT DOCUMENTS

| | | | |
|---|---|---|---|
| 4,859,716 | 8/1989 | Ibsen et al. | 522/14 |
| 4,872,936 | 10/1989 | Engelbrecht | 156/307.3 |
| 4,886,843 | 12/1989 | Walton | 522/174 |
| 4,918,115 | 4/1990 | Jones et al. | 522/144 |
| 4,923,905 | 5/1990 | Masuhara et al. | 522/24 |
| 4,936,775 | 6/1990 | Bennett | 433/220 |
| 4,977,197 | 12/1990 | Sasaki et al. | 522/14 |
| 5,006,340 | 4/1991 | Atsuta et al. | 424/405 |
| 5,008,300 | 4/1991 | Makino et al. | 522/8 |
| 5,015,180 | 5/1991 | Randklev | 433/9 |
| 5,028,638 | 7/1991 | Heid et al. | 522/14 |
| 4,534,839 | 8/1985 | Schaefer | 204/159.23 |
| 4,539,382 | 9/1985 | Omura et al. | 526/276 |
| 4,544,359 | 10/1985 | Waknine | 523/115 |
| 4,544,467 | 10/1985 | Bunker et al. | 204/159.24 |
| 4,547,531 | 10/1985 | Waknine | 523/116 |
| 4,548,689 | 10/1985 | Sakashita et al. | 204/159.23 |
| 4,553,940 | 11/1985 | Koblitz et al. | 523/115 |
| 4,554,336 | 11/1985 | Kidd et al. | 526/301 |
| 4,600,389 | 7/1986 | Schwartz | 433/217.1 |
| 4,650,847 | 3/1987 | Omura et al. | 526/376 |
| 4,668,712 | 5/1987 | Hino et al. | 522/13 |
| 4,674,980 | 6/1987 | Ibsen et al. | 433/228.1 |
| 4,695,251 | 9/1987 | Randklev | 433/8 |
| 4,721,735 | 1/1988 | Bennett et al. | 522/71 |
| 4,744,759 | 5/1988 | Bowen | 433/228.1 |
| 4,746,685 | 5/1988 | Masuhara et al. | 522/13 |
| 4,746,686 | 5/1988 | Waller | 522/14 |
| 4,762,863 | 8/1988 | Sasaki et al. | 522/11 |
| 4,771,084 | 9/1988 | Kubota et al. | 522/10 |
| 4,772,325 | 9/1988 | Kwan et al. | 106/35 |
| 4,801,528 | 1/1989 | Bennett | 433/220 |
| 4,816,495 | 3/1989 | Blackwell et al. | 522/14 |
| 4,820,744 | 4/1989 | Kubota et al. | 522/13 |
| 4,824,876 | 4/1989 | Matsumoto et al. | 522/24 |
| 4,839,401 | 6/1989 | Waknine | 522/14 |

ORTHODONTIC ADHESIVES

BACKGROUND OF THE INVENTION

The present invention relates broadly to dental adhesives and, more specifically, to orthodontic adhesives suitable for use in adhering orthodontic appliances to human teeth.

Prior to the 1970's, orthodontic appliances were commonly attached to teeth by stainless steel bands which circumscribed the entire tooth. These appliances were painful and tedious to fit, and often painful and cumbersome to wear. Furthermore, these appliances quite often resulted in the formation of pre-carious lesions in the tooth enamel beneath the bands during the course of treatment. These lesions were caused because of microleakage of the luring cement used to fill any voids between the band and the tooth surface, due to the impossible difficulties of perfectly adapting the band to the contours of the tooth surface. At this time, orthodontic appliances were developed in the form of buccal, and later also lingual, brackets with flat or slightly contoured bases, which could be adhered to an etched tooth surface with self-curing polymeric resinous adhesives.

Later, in the early 1970's, with the development of the first photocurable dental materials, disclosed in U.S. Pat. Nos. 3,629,187 and 3,709,866, it became possible to utilize photocurable orthodontic adhesives in addition to the self-curing type. The photocured material required that the orthodontic appliances or brackets were sufficiently perforated to permit the rays from the curing light to pass through the bracket, and effect adequate polymerization curing of the adhesive interlayer to ensure strong adherence to the etched tooth surface and to the base of the bracket, since such adherence is only as strong as the weakest interface. U.S. Pat. No. 4,063,360 sets forth an example of the state of the art at this time.

Since the early 1970's, there has been considerable technical progress in all associated areas, including the development, and in many cases, commercialization of new raw materials suitable for the formulation of orthodontic adhesives, the design of orthodontic appliances, and of dental curing lights.

Some of these developments which impact the present invention are the synthesis and commercialization of Ethoxylated Bisphenol A Dimethacrylate resin, the interest in urethane chemistry, which led to the synthesis of the urethane polymethacrylate resins described in U.S. Pat. No. 4,554,336, the development of fluoride leachable glasses described in U.S. Pat. No. 4,746,686, and the synthesis of fluorine-containing adducts such as described in U.S. Pat. No. 4,772,325.

There is a continuing need in the dental field for orthodontic adhesives, both visible light curable and self-curing, which can firmly adhere orthodontic appliances to the dentition, and which provide for a high degree of surface wetting, which contain an available source of leachable fluoride, and which have low polymerization shrinkage and high physical properties. These compositions should include either photoinitiators or self-curing catalysts, and optionally a combination of both, to provide a degree of post-curing capability, together with a polymerizable liquid matrix and a high loading of filler(s) to significantly reduce polymerization shrinkage. They should further provide a thixotropic, taffy-like consistency for optimal manipulation, prior to polymerization curing.

It is therefore an objective of the present invention to provide superior state of the art orthodontic adhesives of both the visible light curable and self-curing types having the properties and advantages described above.

SUMMARY OF THE INVENTION

The present invention is directed to orthodontic adhesive formulations, both light curable in the visible wavelength range, and self-curing, for use in the adherence of orthodontic appliances to the surface of etched human teeth. These formulations exhibit a high degree of surface wetting, an available source of leachable fluoride, low polymerization shrinkage, high physical properties and adhesion, and in the light curable embodiment, a post-curing capability. The essential components of these adhesives include the following:

- A high molecular weight resin or resin blend capable of in-vivo polymerization to a tough, non-brittle polymer to function as the major portion of the liquid matrix of these adhesives.
- A hydrophilic monomer, capable of copolymerization in-vivo with the resin or resin blend described above, which will impart to the liquid matrix of the adhesive, excellent wetting characteristics on all substrates involved.
- A photoinitiation system for visible light curing polymerization or a two-component catalyst system for self-curing orthodontic adhesives, preferably together with a means of providing a degree of post-curing capability in the visible light curable materials.
- An available source of leachable fluoride to provide sustained fluoride release over a lengthy time period without causing significant adhesive solubility in-vivo, such as the monomeric boron trifluoride adducts of the prior art and novel synthesized compositions disclosed herein.
- An adhesive promoting monomer, such as commercially available acrylic functional materials.
- An inert visible light transmitting filler, preferably having a refractive index as close as possible to that of the polymerizable liquid matrix of the visible light curable adhesive for maximum light transmission.

DETAILED DESCRIPTION OF THE INVENTION

The orthodontic adhesives of the present invention can be characterized as tooth-colored, filled, thixotropic polymeric blends of methacrylate functional copolymerizable resins and hydrophilic monomers, optionally including types with chemical bonding functionality, formulated either as photopolymerizable single component pastes, with post-curing capability, or as two-component materials which are autocurable upon mixing.

These adhesives prior to polymerization are honogeneous tacky, viscous pastes, which upon polymerization are rapidly converted to hard resin bonded composites, with high physical properties.

The formulation and concentration ranges for the orthodontic adhesive compositions of the present invention are set forth in Tables I and II for the visible light cured and self-curing embodiments, respectively.

TABLE I
VISIBLE LIGHT CURABLE ORTHODONTIC ADHESIVE

| Formulation | Broad Range Weight Percent | Preferred Range Weight Percent |
|---|---|---|
| Polymerizable Resin Blend | 10–40 | 20–30 |
| Hydrophilic Monomer | 2–15 | 4–10 |
| Photoinitiator | 0.01–1.00 | 0.05–0.50 |
| Synergistic Active Nitrogen Compound | 0.01–1.00 | 0.05–0.50 |
| Post-Curing Promoter | 0.01–1.00 | 0.05–.050 |
| Leachable Fluoride Compound | 0.1–5.0 | 0.2–2.0 |
| Adhesive Promoting Monomer | 0.2–10.0 | 0.5–5.0 |
| Light Transmitting Filler | 10–80 | 30–75 |

TABLE II
SELF-CURING ORTHODONTIC ADHESIVE

| Formulation | Broad Range Weight Percent | Preferred Range Weight Percent |
|---|---|---|
| First Component | | |
| Polymerizable Resin | 10–40 | 20–30 |
| Hydrophilic Monomer | 2–15 | 4–10 |
| Redox Reducing Agent | 0.05–2.0 | 0.1–1.0 |
| Leachable Fluoride Compound | 0.1–5.0 | 0.2–2.00 |
| Adhesive Promoting Monomer | 0.2–10.0 | 0.5–5.0 |
| Filler | 10–80 | 30–75 |
| Second Component | | |
| Polymerizable Resin | 10–40 | 20–30 |
| Hydrophilic Monomer | 2–15 | 4–10 |
| Redox Oxidizing-Agent | 0.05–2.0 | 0.1–1.0 |
| Filler | 10–80 | 30–75 |

More specifically the various components of the present invention comprise the following:

A high molecular weight resin blend capable of polymerization curing to a tough, non-brittle polymer is preferably formed by blending at least one commercially available methacrylate functional resin, such as the adduct of Bisphenol A and Glycidyl Methacrylate, known as BisGMA; Bisphenol A Dimethacrylate; or Ethyoxylated Bisphenol A Dimethacrylate, which all tend to form brittle homopolymers, with either a commercially available methacrylate functional polyurethane resin, of which there are very many, or more preferably a custom synthesized version, such as the examples cited in U.S. Pat. No. 4,554,336, which is incorporated herein by reference, which are known to polymerize to form tougher, less brittle polymers.

The hydrophilic copolymerizable monomer, which is used to impart excellent substrate wetting characteristics to the orthodontic adhesives of the present invention, may be chosen from the group comprising Hydroxypropyl Methacrylate, Hydroxyethyl Methacrylate, Glycerol Dimethacrylate, Glycerol Monomethacrylate, Glycerol Acrylate, Hydroxypropyl Acrylate, Hydroxyethyl Acrylate and any other suitable hydrophilic monomers.

The photoinitiation system for the visible light curing adhesives may comprise any suitable photoinitiator such as 2,3-Bornanedione or Benzil, capable of peak light absorption in the visible wavelength range, and beneficially, a synergistically active nitrogen or nitrogen and sulfur containing compound, such as a suitable tertiary amine or thiazole derivative, plus a means of providing a degree of post-curing capability. OR A two-component catalyst system for the self-curing orthodontic adhesives, which can be based on the redox combination of an acyl peroxide and a tertiary amine, which generate free radicals to initiate polymerization of acrylic functional monomeric compounds by the Imoto mechanism, the interaction of a polymerizable acrylic functional acid, such as acrylic or methacrylic acid, with a stable salt of an unstable acid, such as para toluene sulfinic acid, to generate free radicals for polymerization initiation, or any other suitable free radical generator.

The available source of leachable fluoride is chosen to provide sustained release capability consistent with minimal solubility, from a broad group of commercial available inorganic fluorides, fluorine containing monomers, other organic fluorides and organmetallic fluorides, or especially the Boron Trifluoride adducts described in U.S. Pat. No. 4,772,325, which is incorporated herein by reference.

The adhesive promoting monomer may be chosen from any suitable commercially available acrylic functional materials. Suitable materials include:
Chlorophosphonated BisGMA resin;
Phenylphosphonated Ethyl Methacrylate;
n-Phenyl Glycine-Glycidyl Methacrylate Adduct;
n-Tolyl Glycine-Glycidyl Methacrylate Adduct;
4-Methacryloxyethlyl Trimellitic Anhydride;
Pyromellitic Acid Dimethacrylate and
others of similar chemical functionality, including Glycerophosphate Dimethacrylate.

The finely divided inert visible light transmitting filler is preferably selected for a good refractive index match to the liquid matrix of the light curable orthodontic adhesive. These materials may be selected from the group comprising Poly Bis-GMA Resin, Poly-Ethoxylated Bisphenol A Dimethacrylate Resin, polymerized Polyurethane Dimethacrylate Resins, Poly Bisphenol A Dimethacrylate Resin, Lithium Aluminum Silicate, Barium Aluminum Borosilicate, suitable commercially available glasses, such as Corning 1720 or Ballotini 3100, and many others, including Quartz, and mixtures thereof.

Various ingredients suitable for use with the present invention are commercially available from the following sources:

| Ingredient | Source |
|---|---|
| Ethoxylated Bisphenol A Dimethacrylate | Noury Chemical Corp. 2153 Lockport Olcott Rd. |
| Benzoyl Peroxide | Burt, New York 14028 |
| Urethane Dimethacrylate Resin (U.S. Pat. No. 4,554,336) | Scientific Pharmaceuticals Inc. (Scipharm) 1828 Evergreen Street Duarte, California 91010 |
| Hydroxyethyl Methacrylate | Esschem Company, POB 56 Essington, PA. 19029 |
| 2,3 Bornanedione Mercaptobenzothiazole | Aldrich Chemical Co., Inc. 1001 W. St. Paul Avenue Milwaukee, WI. 53233 |
| Barium Aluminum Borosilicate | Kimble Div. of Owens Illinois Crystal Avenue Drawer 7, Vineland NJ 08360 |
| Glycerophosphate Dimethacrylate | Obtained by special order, No. 1797. from Polysciences, Inc. 400 Valley Road Warrington, PA. 18976 and by special orders No. 73240 from Kerr Mfg. Co., 28200 Wick Rd. Romulus, MI. 48174 |

The following examples illustrate various embodiments of the present invention. The percentages and parts are by weight unless otherwise stated.

EXAMPLE 1

A visible light curable orthodontic adhesive composition is made by the following method. The formulation is made by adding the liquid components to a suitable commercially available planetary mixer, followed by the addition of any soluble ingredients, and mixing until-they are dissolved, after which the fillers are added to complete the paste, which is further mixed until throughly homogeneous. In each of the Examples 1, 2, 3 and 4 the ingredients have been listed in order of mixing using a Ross planetary mixer.

The light curable adhesive has the following composition:

| | Weight Percent | Source |
|---|---|---|
| Urethane Dimethacrylate Resin (U.S. Pat. No. 4,554,336)* | 10.0 | Scipharm |
| Ethoxylated BisPhenol A Dimethacrylate | 10.0 | Noury |
| Hydroxypropyl Methacrylate | 5.0 | Esschem |
| 2,3-Bornanedione | 0.2 | Aldrich |
| Mercaptobenzothiazole | 0.3 | Aldrich |
| DEAEMA. $BF_3$ (U.S. Pat. No. 4,772,325)** | 1.0 | |
| Benzoyl Peroxide | 0.3 | Noury |
| Glycerol Phosphate Dimethacrylate | 1.0 | Polysciences |
| Lithium Aluminum Silicate (Silanated) | 72.2 | Kimble |
| | 100.0 | |

*The Urethane Dimethacrylate Resin used in Examples 1, 2, 3 and 4 of this U.S. Pat. application is prepared in accordance with Example 4 of U.S. Pat. No. 4,544,336 which is incorporated herein by reference.
**The Diethylaminoethylmethacrylate-Borontrifluoride Adduct used in Examples 1, 2, 3 and 4 is the 1:1 Adduct prepared in accordance with Example 2 of U.S. Pat. No. 4,772,325 which is incorporated herein by reference.

The following test results compare the subject adhesive versus two of the better commercially available materials.

The slump test is a measure of consistency and is a good indicator of the adhesive material's ability to hold an attachment where placed (resist drift) prior to polymerization. The shear test directly examines the adhesive's ability to couple an attachment to a tooth enamel surface. In the following examples, all shear testing is performed on etched bovine enamel. A Demetron VCL 300 dental curing lamp having an output of 350 milliwatts per square centimeter was used to cure all light cured specimens. The light was directed atop the bracket in all cases. Two component adhesives for all self cured specimens were mixed at 1:1 weight ratio for 20 seconds, one mix per bracket sample. Initial (3 minutes after end of cure for light cure and 10 min. from the start of mix for self cure) and final (24 hours in 37 degrees centigrade water) shear debonding load is reported in Kilograms of force. All brackets were stainless steel brazed to stainless steel foil/mesh pads, the mesh having a count of 100 openings per inch. All shear testing was performed on an Instron 1122 physical test machine.

Consistency was measured according to a modified ADA Specification No. 8:

| | ADA Spec. No. 8 | Modified Procedure |
|---|---|---|
| Test Spec. Amount | 0.50 ml ± 0.02 ml | 0.10 g ± 0.01 g |
| Total weight | 120 g. | 454 g. |
| Time | 10 min. | 3 min. ± 5 sec. |

1. Slump test consistency of this paste was 13 mm compared with 20 mm for Light Bond ™ (Reliance Products, Inc.) Orthodontic and 26.5 mm for Transbond ™, Unitek/3M Corp. two leading commercially available competitive materials which both allow the placed orthodontic brackets to slide or drift on the prepared tooth surface prior to curing.

When irradiated with a Kerr Command curing light of 18,000 microwatts per sq.cm, output for 10 seconds the composition cured to a Barcol hardness of 90.

2. The shear bond strengths to brackets having 0.097 sq.cm bonding pad area, a 30 second light cure:

| Example 1 | Unitek Transbond ™ |
|---|---|
| 1464 PSI | 1025 PSI |

EXAMPLE 2

A self-curing orthodontic adhesive composition is made by following the method of Example 1. The adhesive has the following composition:

| | Weight Percent | Source |
|---|---|---|
| First Component | | |
| Urethane Dimethacrylate Resin (U.S. Pat No. 4,554,336) | 21.0 | Scipharm |
| Hydroxyethyl Methacrylate | 6.0 | Esschem |
| Dihydroxy Ethyl Paratoluidine | 1.0 | CTC Organics |
| DEAEMA. $BF_3$ (U.S. Pat. No. 4,772,325) | 1.0 | |
| Glycerol Phosphate Dimethacrylate | 1.0 | Polysciences |
| Barium Aluminum Borosilicate (Silanated) | 70.0 | Kimble |
| | 100.0 | |
| Second Component | | |
| Ethoxylated BisPhenol A Dimethacrylate | 22.0 | Noury |
| Hydroxyethyl Methacrylate | 5.6 | Esschem |
| Benzoyl Peroxide | 0.4 | Noury |
| Barium Aluminum Borosilicate (Silanated) | 72.0 | Kimble |
| | 100.0 | |

When mixed in an equivolume ratio, the two components provided a work time of over 1.5 minutes and polymerized to a hard mass within 4.0 minutes, without any significant discoloration.

The following testing was carried out using the self curing (SC) adhesive made by Example 2:

Large pad-initial bond strength. Average debonding pad for brackets having 0.252 sq. cm. pad area.

| | 3M Concise | Reliance Phase II |
|---|---|---|
| Example 2.1 SC | | |
| 24.2 ± 5.4 | 22.5 ± 1.6 | 20.7 ± 5.6 |
| Large pad - final (maximum) bond strength of Example 2 system. | | |
| Example 2.2 SC | | |
| 39.2 ± 10.7 | 34.6 ± 5.8 | 35.8 ± 9.3 |

|  | 3M Concise | Reliance Phase II |
|---|---|---|
| Small pad - initial bond strength. Average debonding load for backets having 0.097 cm. pad area. | | |
| Example 2.3 SC | | |
| 10.9 ± 2.2 | 9.4 ± 1.4 | 9.3 ± 2.6 |
| Small pad - final (maximum) bond strength of Example 2 system. | | |
| Example 2.4 SC | | |
| 16.4 ± 2.4 | 12.0 ± 3.0 | 10.5 ± 2.5 |

EXAMPLE 3

A second visible light curable orthodontic adhesive is made by the method of Example 1. The adhesive has the following composition:

|  | Weight Percent | Source |
|---|---|---|
| Ethoxylated BisPhenol A Dimethacrylate | 10.0 | Noury |
| Urethane Dimethacrylate Resin (U.S. Pat. No. 4,554,336) | 10.0 | Scipharm |
| Hydroxyethyl Methacrylate | 6.0 | Esschem |
| 2,3-Bornanedione | 0.2 | Aldrich |
| Mercaptobenzothiazole | 0.3 | Aldrich |
| Benzoyl Peroxide | 0.3 | Noury |
| DEAEMA. BF$_3$ (U.S. Pat No. 4,772,325) | 1.0 | |
| Barium Aluminum Borosilicate | 72.2 | Kimble |
|  | 100.0 | |

When irradiated with a curing light of 18,000 microwatts per sq.cm, output for 10 seconds the composition cured to a Barcol Hardness of 85. The light cured (LC) composition of Example 3 is tested as follows:

Example 3.1

The above composition was further tested as an adhesive for large pad orthodontic brackets, with the initial bond strength being determined. Average debonding load for brackets having bonding pads of 0.252 sq.cm area, 30 second light cure.

| EXAMPLE 3LC | UNITEK TRANSBOND | RELIANCE LIGHT BOND |
|---|---|---|
| 20.5 ± 2.1 kg (1157 PSI) | 12.4 ± 5.6 kg (700 PSI) | 6.5 ± 2.6 kg (367 PSI) |
| EXAMPLE 3.2 | | |
| Large pad - final (maximum) bond strength of Example 3 system. 30 seconds light cure. | | |
| 28.4 ± 3.2 kg (1603 PSI) | 23.8 ± 5.6 kg (1343 PSI) | 14.4 ± 5.1 kg (813 PSI) |

Example 3.3

Small pad-initial bond strength. Average debonding load for brackets having 0,097 sq.cm. bonding pad area, 30 second light cure.

| EXAMPLE 3LC | UNITEK TRANSBOND | RELIANCE LIGHT BOND |
|---|---|---|
| 10.8 ± 1.2 (1583 PSI) | 8.3 ± 3.0 (1217 PSI) | 6.0 ± 1.0 (880 psi) |
| EKAMPLE 3.4 | | |
| Small pad - final (maximum) bond strength of Example 3 system: | | |
| 12.6 ± 3.3 | 10.8 ± 3.0 | 9.0 ± −4.3 |

| EXAMPLE 3LC | UNITEK TRANSBOND | RELIANCE LIGHT BOND |
|---|---|---|
| (1847 PSI) | (1583 PSI) | (1451 PSI) |

Example 3.5

Medium pad 15, 20, and 30 second exposure time-initial bond strength. Average for brackets having 0.194 sq.cm. bonding pad area.

| EXAMPLE 3LC | | | UNITEK TRANSBOND |
|---|---|---|---|
| 15 sec | 20 sec | 30 sec | 30 sec |
| 8.6 ± 1.1 (629 PSI) | 13.7 ± 1.3 (1003 PSI) | 15.1 ± 3.4 (1105 PSI) | 9.3 ± 1.6 (681 PSI) |

EXAMPLE 4

A second self-curing orthodontic adhesive composition is made by the method of Example 2. The adhesive has the following composition:

|  | Weight Percent |
|---|---|
| First Component | |
| Urethane Dimethacrylate Resin (U.S. Pat. No. 4,554,336) | 21.0 |
| Hydroxypropyl Methacrylate | 6.0 |
| Dihydroxy Ethyl Paratoluidine | 1.0 |
| DEAEMA. BF$_3$ (U.S. Pat. No. 4,772,325) | 1.0 |
| Glycerol Phosphate Dimethacrylate | 1.0 |
| Quartz (silanated) | 70.0 |
|  | 100.0 |
| Second Component | |
| Ethoxylated BisPhenol A Dimethacrylate | 22.0 |
| Hydroxypropyl Methacrylate | 5.6 |
| Benzoyl Peroxide | 0.4 |
| Quartz (Silanated) | 72.0 |
|  | 100.0 |

When mixed in an equivolume ratio, the two components of the above composition provided a work time of over 1.5 minutes and polymerized to a hard mass within 4.0 minutes, without any significant discoloration.

It can be seen from the above comparative test results that the adhesives of the present invention offer superior bond strength over the best available commercial materials. Of particular importance is the crucial initial bond strength, the time at which most bond failures occur. These adhesives provide the improved level of adhesion necessary for successful orthodontic bonding.

Although particular embodiments of the present invention have been disclosed herein for purposes of explanation, further modifications or variations thereof will be apparent to those skilled in the art to which this invention pertains.

What is claimed:

1. A visible light curable orthodontic adhesive that comprises a high molecular weight resin or resin blend which is photocurable to form a tough, non-brittle polymer, blended with a hydrophilic copolymeric monomer which provides excellent substrate wetting characteristics;
   an adhesion promoting monomer;
   a photoinitiator;
   a synergistic reducing agent;

a component which provides for a source of leachable fluoride;

an acyl peroxide capable of providing post-curing characteristics; and a filler or fillers in the form of inert, finely divided visible light transmitting material.

2. The composition of claim 1 in which the resin blend comprises at least one methacrylate functional resin and at least one methacrylate functional polyurethane resin.

3. The composition of claim 1 in which the hydrophilic substrate wetting monomer is at least one selected from the group consisting of hydroxypropyl methacrylate, hydroxyethyl methacrylate, glycerol dimethacrylate, glycerol monomethacrylate, glycerol acrylate, hydroxpropyl acrylate and hydroxyethyl acrylate.

4. The composition of claim 1 in which the leachable fluoride component comprises a diethylaminoethylmethacrylate-borontrifluoride adduct.

5. The composition of claim 1 in which the adhesive promoting monomer comprises a phosphate functional methacrylate monomer.

6. A two-component orthodontic adhesive that comprises in the first component a high molecular weight resin or resin blend, together with a hydrophilic monomer, an adhesion promoting monomer, a component which provides a source of leachable fluoride, a self-curing initiator, and a filler or fillers in the form of inert, finely divided particles; and as the second component, a high molecular weight resin or resin blend, together with a hydrophilic monomer, a self-curing catalyst, a filler or fillers in the form of inert, finely divided particles, and a small amount of color masking pigment.

7. The composition of claim 6 in which the resin blend of the first component comprises at least one methacrylate functional resin, which can be beneficially a methacrylate functional polyurethane resin.

8. The composition of claim 6 in which the hydrophilic substrate wetting monomer is at least one selected from the group consisting of hydroxypropyl methacrylate, hydroxyethyl methacrylate, glycerol dimethacrylate, glycerol monomethacrylate, glycerol acrylate, hydroxypropyl acrylate and hydroxyethyl acrylate.

9. The composition of claim 6 in which the resin blend of the second component comprises at least one methacrylate functional resin.

10. The composition of claim 6 in which the leachable fluoride component comprises a diethylaminoethylmethacrylate-borontrifluoride adduct.

11. The composition of claim 6 in which the adhesive promoting monomer comprises a phosphate functional methacrylate monomer.

12. A visible light curable orthodontic adhesive, in the form of a single paste component, which comprises the following ingredients in weight per cent:

|  | Concentration |
|---|---|
| Polymerizable Resin Blend | 10–40 |
| Hydrophilic Monomer | 2–15 |
| Photoinitiator | 0.01–1.00 |
| Synergistic Active Nitrogen Compound | 0.01–1.00 |
| Post-curing promoter | 0.01–1.00 |
| Leachable Fluoride Compound | 0.01–5.0 |
| Adhesion Promoting Monomer | 0.2–10.00 |
| Light Transmitting Filler | 10–80. |

13. A visible light curable orthodontic adhesive, in the form of a single paste component which comprises the following ingredients in weight per cent:

|  | Concentration |
|---|---|
| Polymerizable Resin Blend | 20–30 |
| Hydrophilic Monomer | 4–10 |
| Photoinitiator | 0.05–0.50 |
| Synergistic Active Nitrogen Compound | 0.05–0.50 |
| Post-curing promoter | 0.05–0.55 |
| Leachable Fluoride Compound | 0.02–2.0 |
| Adhesion Promoting Monomer | 0.5–5.0 |
| Light Transmitting Filler | 30–75. |

14. A self-curing orthodontic adhesive in two component form, comprising the following ingredients in weight per cent:

|  | Concentration |
|---|---|
| First Component |  |
| Polymerizable Resin | 10–40 |
| Hydrophilic Monomer | 2–15 |
| Redox Reducing Agent | 0.05–2.0 |
| Leachable Fluoride Compound | 0.1–5.0 |
| Adhesion Promoting Monomer | 0.2–10.0 |
| Filler | 10–80 |
| Second Component |  |
| Polymerizable Resin | 10–40 |
| Hydrophilic Monomer | 2–15 |
| Redox oxidizing Agent | 0.05–2.0 |
| Filler | 10–80. |

15. A self-curing orthodontic adhesive, in two component form, comprising the following ingredients in weight per cent:

|  | Concentration |
|---|---|
| First Compound |  |
| Polymerizable Resin | 20–30 |
| Hydrophilic Monomer | 4–10 |
| Redox Reducing Agent | 0.01–1.0 |
| Leachable Fluoride Compound | 0.2–2.0 |
| Adhesion Promoting Monomer | 0.5–5.0 |
| Filler | 30–75 |
| Second Component |  |
| Polymerizable Resin | 20–30 |
| Hydrophilic Monomer | 4–10 |
| Redox Oxidizing Agent | 0.1–1.0 |
| Filler | 30–75. |

16. A single component visible light curable orthodontic adhesive having the following composition:

|  | Weight Percent |
|---|---|
| Ethoxylated BisPhenol A Dimethacrylate | 10.0 |
| Urethane Dimethacrylate Resin | 10.0 |
| Hydroxyethyl Methacrylate | 6.0 |
| 2,3-Bornanedione | 0.2 |
| Mercaptobenzothiazole | 0.3 |
| Benzoyl Peroxide | 0.3 |
| DEAEMA. BF$_3$ | 1.0 |
| Barium Aluminum Borosilicate (Silanated) | 72.2 |
|  | 100.0. |

17. A self-curing two component orthodontic adhesive having the following composition:

|  | Weight Percent |
|---|---|
| First Component | |
| Urethane Dimethacrylate Resin | 21.0 |
| Hydroxyethyl Methacrylate | 6.0 |
| Dihydroxy Ethyl Paratoluidine | 1.0 |
| DEAEMA. BF$_3$ | 1.0 |
| Glycerol Phosphate Dimethacrylate | 1.00 |
| Barium Aluminum Borosilicate (Silanated) | 70.0 |
| | 100.0 |
| Second Component | |
| Ethoxylated BisPhenol A Dimethacrylate | 22.0 |
| Hydroxyethyl Methacrylate | 5.6 |
| Benzoyl Peroxide | 0.4 |
| Barium Aluminum Borosilicate (Silanated) | 72.0 |
| | 100.0. |

* * * * *